United States Patent
Johnson et al.

(10) Patent No.: US 8,414,658 B2
(45) Date of Patent: Apr. 9, 2013

(54) ANATOMICALLY-CONFIGURED ADJUSTABLE UPPER EXTREMITY PROSTHETIC DEVICE

(75) Inventors: Alwyn P. Johnson, Littleton, CO (US); Bradley D. Veatch, Westminster, CO (US); Norman J. Haberkorn, Parker, CO (US); Ronald Krenzel, Frederick, CO (US)

(73) Assignee: Invisible Hand Enterprises, LLC, Westminster, CO (US)

( * ) Notice: Subject to any disclaimer, the term of this patent is extended or adjusted under 35 U.S.C. 154(b) by 562 days.

(21) Appl. No.: 12/572,112

(22) Filed: Oct. 1, 2009

(65) Prior Publication Data
US 2010/0082116 A1    Apr. 1, 2010

Related U.S. Application Data

(60) Provisional application No. 61/101,892, filed on Oct. 1, 2008.

(51) Int. Cl.
*A61F 2/56* (2006.01)
*A61F 2/78* (2006.01)

(52) U.S. Cl. ............................................ 623/32; 623/57
(58) Field of Classification Search ............... 623/57, 623/32
See application file for complete search history.

(56) References Cited

U.S. PATENT DOCUMENTS

| | | | |
|---|---|---|---|
| 1,183,413 A | 5/1916 | Visel | |
| 1,378,578 A | 5/1921 | Bauman | |
| 1,390,802 A | 9/1921 | McKay | |
| 1,465,933 A | 8/1923 | Dedic | |
| 1,466,487 A | 8/1923 | Shaffer | |
| 1,608,689 A | 11/1926 | Apel | |
| 1,819,317 A | 8/1931 | Baehr | |
| 1,981,698 A | 11/1934 | Henning | |
| 2,098,481 A | 11/1937 | Baird | |

(Continued)

FOREIGN PATENT DOCUMENTS

| CA | 2 325 607 A1 * | 5/2002 |
|---|---|---|
| DE | 901583 | 1/1954 |

(Continued)

OTHER PUBLICATIONS

International Preliminary Report on Patentability for International (PCT) Patent Application No. PCT/US2009/059179, mailed Apr. 14, 2011 7 pages.
"The Open Prosthetics Project: A Versatile Body-Powered Hand", available at http://openprosthetics.org/body-powered, printed May 7, 2009, pp. 1-5.
Amstead, B.H., et al.; "Manufacturing Processes, 7th Ed."; John Wiley & Sons, New York, 1977, pp. 269-270.

(Continued)

*Primary Examiner* — David H. Willse
(74) *Attorney, Agent, or Firm* — Sheridan Ross P.C.

(57) ABSTRACT

An upper extremity prosthetic device is provided that comprises three main components, namely, an arm cuff, a forearm section and a distal connector. The arm cuff is adjustable to accommodate lower arms of different sizes. The forearm section may be constructed in certain limited sizes to accommodate different sized forearm residual limbs. The distal connector is designed to connect to any of the forearm section configurations, and the distal connector enables any terminal device to be attached to the connector. The components may be mixed and matched in various combinations to fit the physical dimensions of virtually any amputee. The interchangeable parts will accommodate a wide range of residual limb geometries, overall sizes and lengths. Embodiments of the present invention minimize the need for time and resource-intensive customized fitting and create an affordable, relatively low-cost prosthetic interface.

19 Claims, 9 Drawing Sheets

U.S. PATENT DOCUMENTS

| | | | |
|---|---|---|---|
| 2,382,403 | A | 8/1945 | Eberle |
| 2,409,884 | A | 10/1946 | Mollenhour |
| 2,549,074 | A | 4/1951 | Fishbein et al. |
| 2,561,383 | A | 7/1951 | Larkins et al. |
| 2,573,351 | A | 10/1951 | Motis |
| 2,582,234 | A | 1/1952 | Conzelman, Jr. et al. |
| 2,638,604 | A | 5/1953 | Motis |
| 2,641,769 | A | 6/1953 | Robinson |
| 2,669,728 | A * | 2/1954 | Ritchie ............... 623/57 |
| 2,692,390 | A | 10/1954 | Motis |
| 2,710,974 | A | 6/1955 | Motis |
| 3,258,784 | A | 7/1966 | Brown |
| 3,604,017 | A | 9/1971 | Brown et al. |
| 3,888,362 | A | 6/1975 | Fletcher et al. |
| 3,932,045 | A | 1/1976 | Hillberry et al. |
| 3,945,053 | A | 3/1976 | Hillberry et al. |
| 4,225,983 | A | 10/1980 | Radocy et al. |
| 4,258,441 | A | 3/1981 | Bell |
| 4,332,038 | A | 6/1982 | Freeland |
| 4,373,517 | A | 2/1983 | Criscuolo |
| 4,377,305 | A | 3/1983 | Horvath |
| 4,503,590 | A | 3/1985 | Girard |
| 4,792,338 | A | 12/1988 | Rennerfelt |
| 4,834,760 | A | 5/1989 | Richter |
| 4,865,613 | A | 9/1989 | Rizzo |
| 4,923,477 | A | 5/1990 | Horvath |
| 4,990,162 | A | 2/1991 | LeBlanc et al. |
| 5,116,386 | A | 5/1992 | Scribner |
| 5,219,366 | A | 6/1993 | Scribner |
| 5,549,636 | A | 8/1996 | Li |
| 5,597,189 | A | 1/1997 | Barbee, Sr. |
| 5,784,979 | A | 7/1998 | Nelson |
| 5,888,235 | A | 3/1999 | Jacobsen et al. |
| 6,010,536 | A | 1/2000 | Veatch |
| D460,858 | S | 7/2002 | Zebe, Jr. |
| 6,443,032 | B1 | 9/2002 | Fujii et al. |
| 6,447,532 | B1 | 9/2002 | Herder et al. |
| 6,605,118 | B2 | 8/2003 | Capper et al. |
| 7,083,584 | B2 | 8/2006 | Coligado |
| 7,150,078 | B2 | 12/2006 | Gijsel et al. |
| 7,341,295 | B1 | 3/2008 | Veatch |
| 7,361,197 | B2 | 4/2008 | Winfrey |
| 1,042,413 | A1 | 10/2012 | Dorrance |
| 2004/0195883 | A1 | 10/2004 | Vrijlandt et al. |
| 2005/0192676 | A1 | 9/2005 | Sears et al. |
| 2005/0216097 | A1 | 9/2005 | Rifkin |
| 2005/0234564 | A1 | 10/2005 | Fink et al. |
| 2006/0112619 | A1 | 6/2006 | Oderwald et al. |
| 2007/0032884 | A1 | 2/2007 | Veatch |
| 2007/0213842 | A1 | 9/2007 | Simmons |
| 2008/0188952 | A1 | 8/2008 | Veatch |
| 2009/0287316 | A1 | 11/2009 | Veatch et al. |

FOREIGN PATENT DOCUMENTS

| | | |
|---|---|---|
| GB | 126457 | 5/1919 |
| NL | 1009886 | 2/2000 |
| WO | WO 98/11833 | 3/1998 |
| WO | WO 03/017880 | 3/2003 |
| WO | WO 2004/023863 | 3/2004 |

OTHER PUBLICATIONS

Atkins, Diane J., et al.; "Comprehensive Management of the Upper-Limb Amputee"; Chapters 5, 11 and 18; New York Springer-Verlag New York, Inc.; 1989.

Cook, R.D., "Concepts and Applications of Finite Element Analysis, 2nd Ed."; John Wiley & Sons, New York, 1981, pp. 483.

Cook, Theodore A., The Curves of Life, Dover Publications, Inc., New York, NY, 1979; republish of original issued by Constable & Co., London, 1914; pp. 407-432.

Cupo et al.; "Clinical Evaluation of a New, Above-Elbow, Body-Powered Prosthetic Arm: A Final Report"; Journal of Rehabilitation Research and Development; vol. 35, No. 4, Oct. 1998; pp. 431-446.

Den Boer et al. (1999) "Sensitivity of laparoscopic dissectors, what can you feel?" Surgical Endoscopy, vol. 13, pp. 869-873.

Frey, DD and Carlson, LE, "A Body-Powered Prehensor with Variable Mechanical Advantage"; Prosthetics and Orthotics International, 1994, 18, 118-123.

Frey, DD, et al., "Voluntary-Opening Prehensors with Adjustable Grip Force"; Journal of Prosthetic and Orthotics; vol. 7, No. 4, Fall 1995, pp. 124-130.

Herder JL (1998) "Design of spring force compensation systems", Mechanism and Machine Theory, 33(1-2)151-161 (Abstract only).

Jaspers et al. (2004) "Camera and Instrument Holders and Their Clinical Value in Minimally Invasive Surgery", Surgical Laparoscopy, Endoscopy & Percutaneous Techniques, 14(3)145-52. (Abstract only).

Jaspers et al., (2004) "Mechanical manipulator for intuitive control of endoscopic instruments with seven degrees of freedom", Minimally Invasive Therapy and Allied Technologies, 13(3)191-8 (Abstract only).

Jobin et al., "An Underactuated Prosthesis Finger Mechanism with Rolling Joints", Proceedings of DETC ASME Design Engineering Technical Conferences and Computers and Information in Engineering Conference, Salt Lake City, Utah, Sep. 28-Oct. 2, 2004, DETC2004-57192, pp. 1-11.

Klopsteg, PE, and Wilson, PD (1968); "Human Limbs and Their Substitutes"; New York: Hafner Publishing Co.; pp. 226-229.

Kruit, J, and Cook, JC, "Body-Powered Hand Prosthesis with Low Operating Power for Children"; Journal of Medical Engineering & Technology; vol. 13, No. 1/2, (Jan./Apr. 1989), pp. 129-133.

Landsberger, S, et al. "Child Prosthetic Hand Design: No Small Challenge"; Proceedings of the 1996 Wescon Conference, Wescon, Los Angeles, CA, 1996:236-240.

LeBlanc, M, et al., "Mechanical Work Efficiencies of Body-Powered Prehensors for Young Children"; Journal of the Association of Children's Prosthetic-Orthotic Clinics, vol. 27, No. 3, Winter 1992:70-75.

Meeks, D., and LeBlanc, M., "Preliminary Assessment of Three New Designs of Prosthetic Prehensors for Upper Limb Amputees"; Prosthetics and Orthotics International, 1988, vol. 12, 41-45.

Melendez, D., and LeBlanc, M., "Survey of Arm Amputees Not Wearing Prostheses: Implications for Research and Service"; Journal of the Association of Children's Prosthetics-Orthotics Clinics; vol. 23, No. 3, Autumn 1988; 8 pp.

Miguelez et al., "The Transradial Anatomically Contoured (TRAC) Interface: Design Principles and Methodology," Journal of Orthotists and Prosthetists, vol. 15(4), 2003, pp. 148-157.

Northwestern University REP-PRL/Resource Unit, "What Users Want: 1992 Survey and Results," Capabilities, vol. 2, No. 4, Jan. 1993, 15 pp.

Plettenburg, DH and Herder, JL; "Voluntary Closing: A Promising Opening in Hand Prosthetics"; Technology and Disability; 15, 2003:85-94.

Rosenbaum DA, "Human Motor Control, 1st Ed."; San Diego: Academic Press; 1991:43.

Sears, H., "Evaluation and Development of a New Hook-Type Terminal Device"; PhD Dissertation Dept. of Bioengineering, University of Utah, Jun. 1983.

Tuijthof et al. (2000) "Design, actuation and control of an anthropomorphic robot arm", Mechanism and Machine Theory 35(7); 945-962 (Abstract only).

Tuijthof et al., "Ergonomic handle for an arthroscopic cutter", Minim Invasive Ther Allied Technol. Mar 2003;12(1):82-90 (Abstract only).

U.S. Department of Health and Human Services Publication FDA 87-4222; "An Introduction to Medical Device Regulations"; pp. 2-3.

Veatch; "A Combination VO/VC Terminal Device with Variable Mechanical Advantage"; ADA Technologies, Inc.; Littleton, Colorado, Feb. 28, 2004; 5 pp.

Visser et al. (2000) "Force directed design of a voluntary closing hand prosthesis", Journal of Rehabilitation Research and Development 37(3)261-271 (Abstract only).

International Search Report for International (PCT) Patent Application No. PCT/US09/59179, mailed Nov. 25, 2009.

Written Opinion for International (PCT) Patent Application No. PCT/US09/59179, mailed Nov. 25, 2009.

* cited by examiner

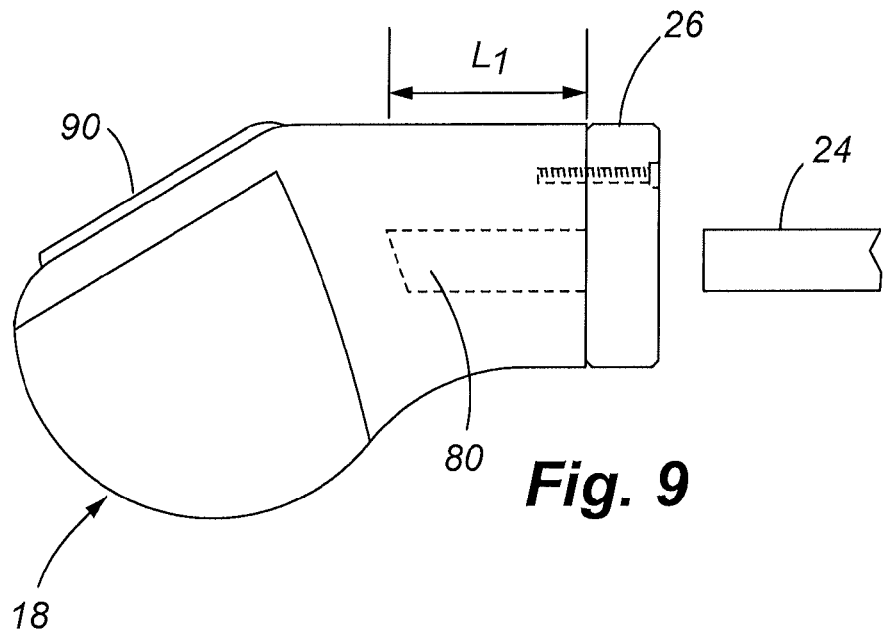
Fig. 9
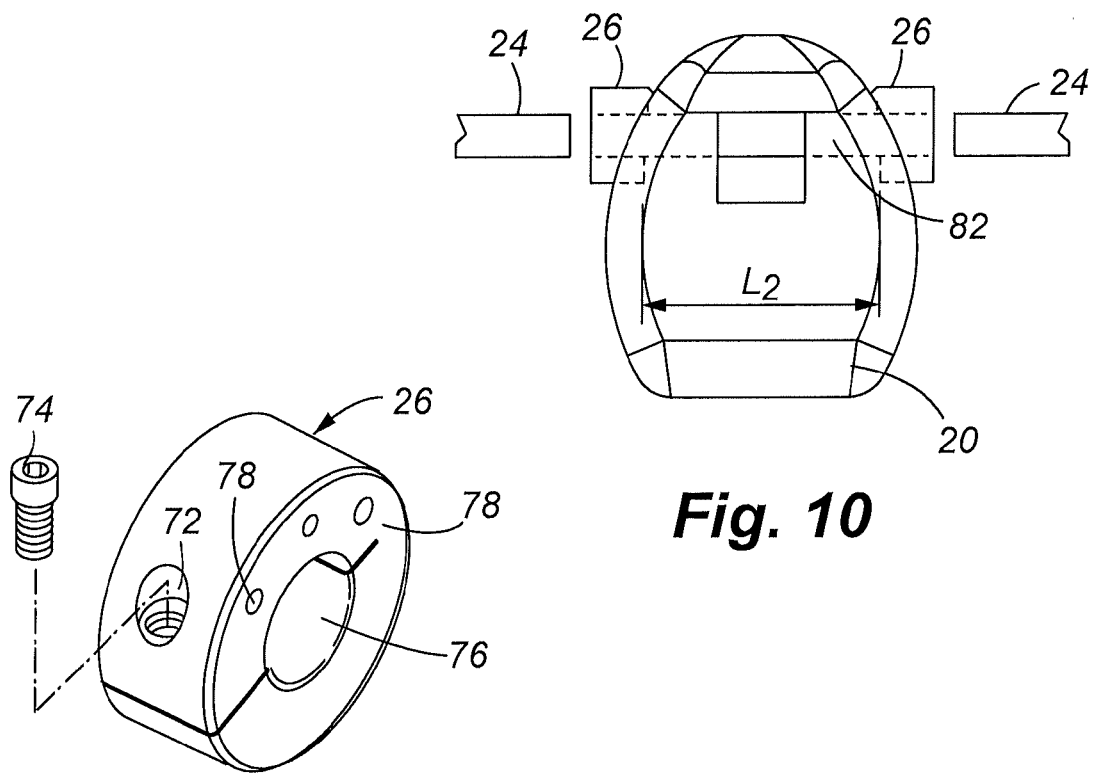
Fig. 10
Fig. 8

ANATOMICALLY-CONFIGURED ADJUSTABLE UPPER EXTREMITY PROSTHETIC DEVICE

CROSS REFERENCE TO RELATED APPLICATION

The present application claims the benefits of U.S. Provisional Application Ser. No. 61/101,892 filed Oct. 1, 2008 entitled "Anatomically-Configured Adjustable Upper Extremity Prosthetic Interface," which is incorporated herein by this reference in its entirety.

FIELD OF THE INVENTION

The present invention relates to an upper extremity prosthetic device for persons with upper extremity transradial (i.e., below elbow) amputations.

BACKGROUND OF THE INVENTION

Presently, many upper extremity prosthetic devices are custom made. In a typical manufacturing process, a cast is made of the amputee's residual limb. A prosthetic device is then molded from the casting. This process is time-consuming and costly. It further requires highly trained individuals to build and fit the devices. As a result, persons with low income and people in most developing countries have no access to such custom fitted devices much less the ability to pay for such devices. Thus, many people are deprived of the benefit of a prosthetic device. In addition, even those persons who can afford an expensive, customized prosthetic device do not participate in a wide variety of activities, such as sporting events, due to concerns over damage to their prosthetic device.

One example of an upper extremity prosthetic device is disclosed in the U.S. Pat. No. 5,888,235. The invention is a prosthetic arm mountable on a socket attached to the residual limb of a person. The prosthetic arm includes a base for attachment to the socket, a forearm section or adapter having a proximal end and a distal end, a terminal device such as a hook or anthropomorphic hand, and attached to the distal end of the forearm section or adapter for selectively opening or closing. An elbow joint interconnects the proximal end of the forearm section to the base, the elbow joint being pivotable to enable moving the forearm section upwardly or downwardly. Control straps and cables fitted on the person are responsive to body movements of the person for selectively locking the elbow joint to prevent it from pivoting while allowing the terminal device to open or close or locking the terminal device to prevent it from opening or closing while allowing the elbow joint to pivot.

Another example of a prosthetic arm is disclosed in the U.S. Patent Application Publication No. 20070213842. This invention comprises a forearm section adapted to mount to the arm of a patient, a hand section including a thumb and at least one finger, and a wrist section connected between the forearm section and said hand section. Movement of the prosthesis is achieved by a combination of pressurized air bladders and return springs. The prosthetic device is structurally and functionally interconnected to simulate a large number of the movements performed by the corresponding natural skeletal structures.

Although there may be a number of differing constructions for arm prosthetic devices, there is still a need to provide an upper extremity prosthetic device that is adjustable to fit persons of different sizes, provides an adjustable fit for a wearer over time, yet provides superior ability for the device to act as a functional prosthesis. There is also a need to provide a prosthetic device for the arm that is relatively inexpensive, yet provides a comfortable and durable solution for the amputee. There is yet another need to provide a prosthetic device that is non-obtrusive to the amputee and provides a natural appearance of a substitute limb.

SUMMARY

In one preferred embodiment of the present invention, the upper extremity prosthetic device, also known as a Johnson Veatch Device, comprises three main components, namely, a lower arm cuff or humeral cuff, a forearm section and a distal connector. The lower arm cuff is adjustable to accommodate lower arms of different sizes. Similarly, the forearm section may be constructed in certain limited sizes, for example, small, medium and large, to accommodate different sized forearm residual limbs. The distal connector is designed to connect to any of the forearm section configurations.

The lower arm cuff comprises two opposed condyle contacts, an olecranon contact, and a posterior humeral contact. A pair of curved rods interconnects the condyle contacts to opposing sides of a base of the cuff. The base can be defined as the olecranon contact and posterior humeral contact that form one integral piece. Four shaft collars are provided in which one shaft collar is disposed on the end of each condyle contact and one each on opposite sides of the olecranon contact. A pair of cable or rod connections interconnects the lower arm cuff to the forearm section.

The forearm section comprises two symmetrically opposed half-shells, a tongue disposed between one side of the half shells, a rear sizing plate disposed between the other side of the half shells, and a plurality of adjustment straps.

The distal connector includes a pair of arms that extend outwardly and interface with matching ends of the forearm section. The distal connector further includes an angled lower surface with a threaded boss for interconnection with a variety of terminal devices. The lower surface may be angled to facilitate positioning of terminal devices relative to the user's body.

The components may be mixed and matched in various combinations to fit the physical dimensions of virtually any amputee. The interchangeable parts will accommodate a wide range of residual limb geometries, overall sizes and lengths. By doing so, embodiments of the present invention will minimize the need for time and resource-intensive customized fitting and, as a result, will create an affordable, relatively low-cost prosthetic interface.

In another aspect of the invention, means are provided for attaching to an arm a plurality of supporting contacts to interconnect the arm to the prosthetic device. The means for attaching comprises a pair of opposing condyle contacts, an olecranon contact, and a posterior humeral contact, said contacts each making contact with the arm thereby providing a suspended configuration for the prosthetic device.

In yet another aspect of the invention, the invention has utility in sub-combination in that the group of four contacts provides an effective device to attach a number of different forearm extensions and terminal devices.

Other features and advantages of the present invention will become apparent from a review of the following Detailed Description taken in conjunction with the Drawings.

BRIEF DESCRIPTION OF THE DRAWINGS

FIG. 8 is a perspective view of a shaft collar of the present invention.

FIG. 9 is a front plan view of a condyle contact of the present invention.

FIG. 10 is a rear elevation view of an olecranon contact of the present invention.

While the following disclosure describes the invention in connection with those embodiments presented, one should understand that the invention is not strictly limited to these embodiments. Furthermore, one should understand that the drawings are not necessarily to scale, and that in certain instances, the disclosure may not include details which are not necessary for an understanding of the present invention, such as conventional details of fabrication and assembly.

DETAILED DESCRIPTION OF THE INVENTION

Figure 1:
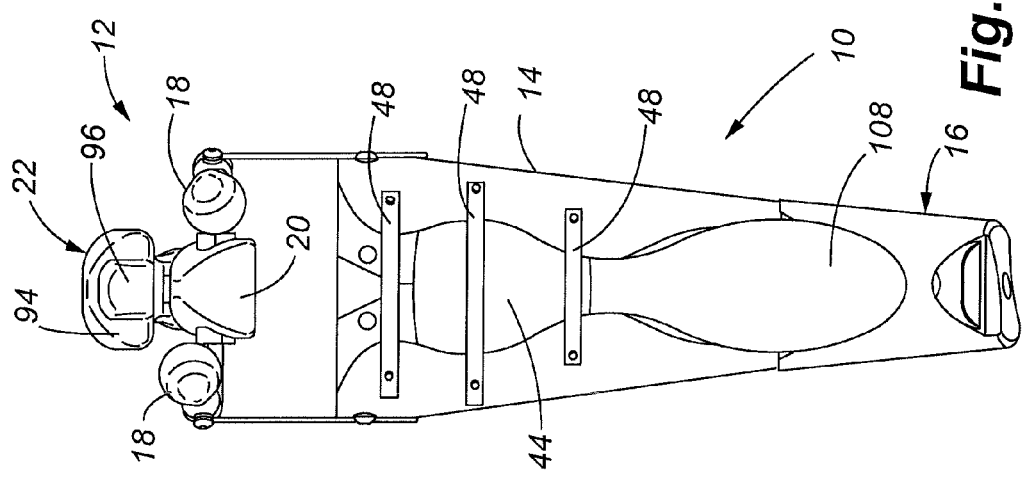
FIG. 1 is front plan view of one embodiment of the lower arm prosthetic device of the present invention.

With reference to FIG. 1, a first embodiment of the upper extremity prosthetic device 10 of the present invention is shown. The upper extremity prosthetic device comprises three portions: A lower arm cuff 12, a forearm section or adapter 14, and a distal connector 16. The prosthetic device 10 is designed to secure to the residual limb of a below-elbow amputee as discussed in more detail below.

Figure 2:
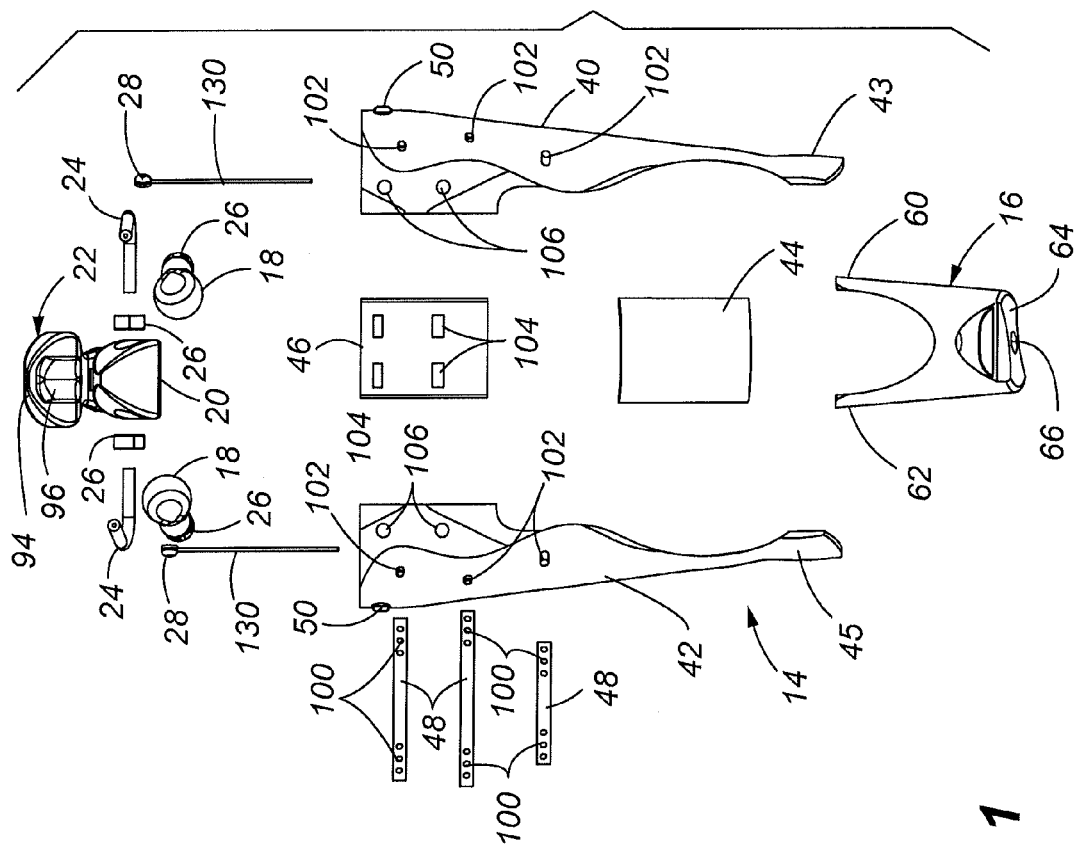
FIG. 2 is an exploded view of the embodiment shown in FIG. 1.

As seen in FIG. 2, the lower arm cuff comprises two opposed condyle contacts 18, an olecranon contact 20, a posterior humeral contact 22, a pair of curved rods 24, four shaft collars 26 (one shaft collar disposed on the end of each condyle contact 18 and one each on opposite sides of the olecranon contact), and a pair of cable or rod connectors 28 associated with the condyle contacts 18.

The forearm section 14 comprises two symmetrically opposed half-shells 40 and 42, a tongue 44, a rear sizing plate 46, and a plurality of adjustment straps 48. Each forearm half-shell 40, 42 further include a cable or rod connector 50 mounted on proximal ends of the half-shells. A pair of cables or rods 130 interconnects the lower arm cuff to the forearm section in which the cables 130 are secured at their respective ends to the connectors 28 and 50.

Figure 3:
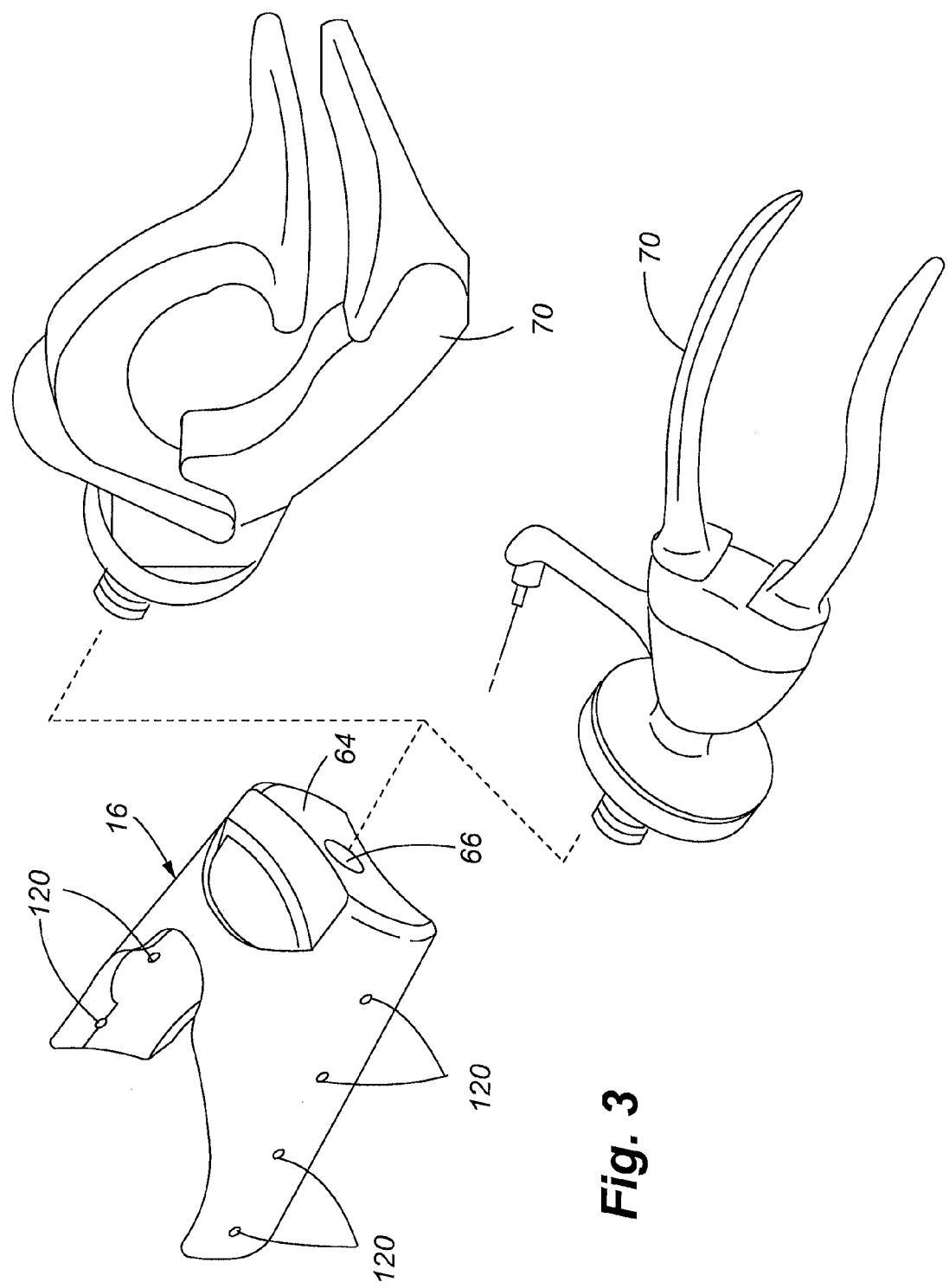
FIG. 3 is a perspective view of a distal connector and exemplary terminal devices.
Figure 5:
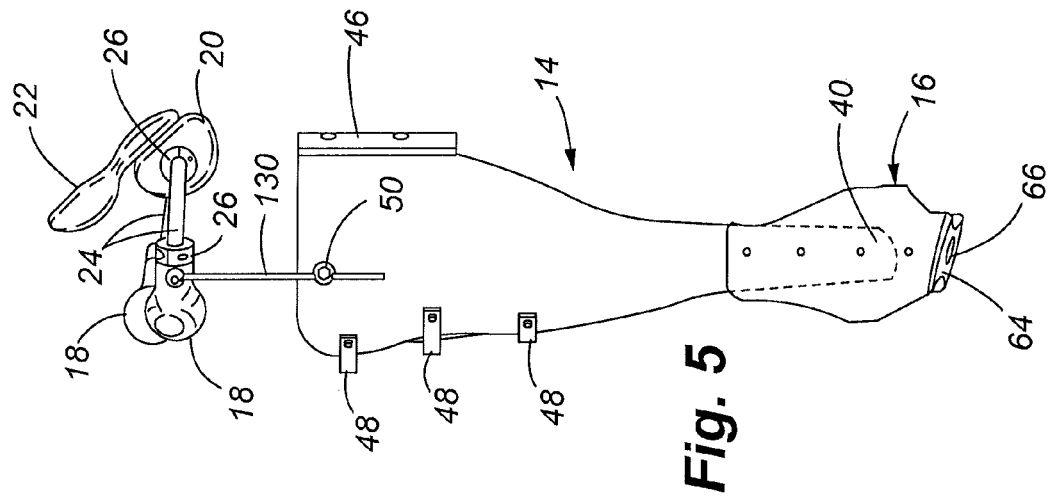
FIG. 5 is an opposite side view of the embodiment of FIG. 1.
Figure 4:
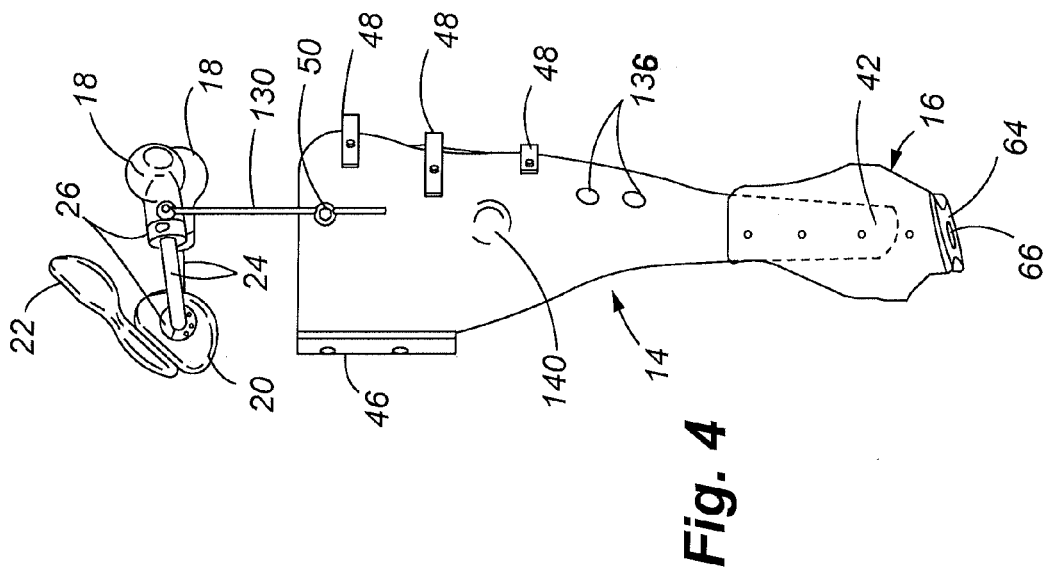
FIG. 4 is a side plan view of the embodiment of FIG. 1.

The distal connector 16 includes a pair of arms 60 and 62 which extend outwardly and interface with distal ends 43 and 45 of the forearm half shells 40 and 42, respectively. The distal connector further includes an angled lower surface 64 with a universally sized threaded boss 66 for interconnection with a variety of terminal devices, exemplary versions of which are shown in FIG. 3. The lower surface 64 extends at an angle, as shown in FIGS. 4 and 5, to facilitate positioning of terminal devices 70 relative to the user's body. For example, the angled lower surface 64 orients a terminal device in a more favorable position for the wearer of the lower arm prosthetic device by orienting the terminal device toward the centerline of the wearer's body. This orientation of the terminal device facilitates, for example, better positioning of grasping food in which the wearer can move the prosthesis to the mouth without undue movement of the head. FIG. 4 is representative of the lower arm prosthetic device 10 as worn on a user's left arm, and FIG. 5 is representative of a lower arm prosthetic device that is worn on a user's right arm, noting how the angled lower surfaces orient the terminal devices.

Figure 6:
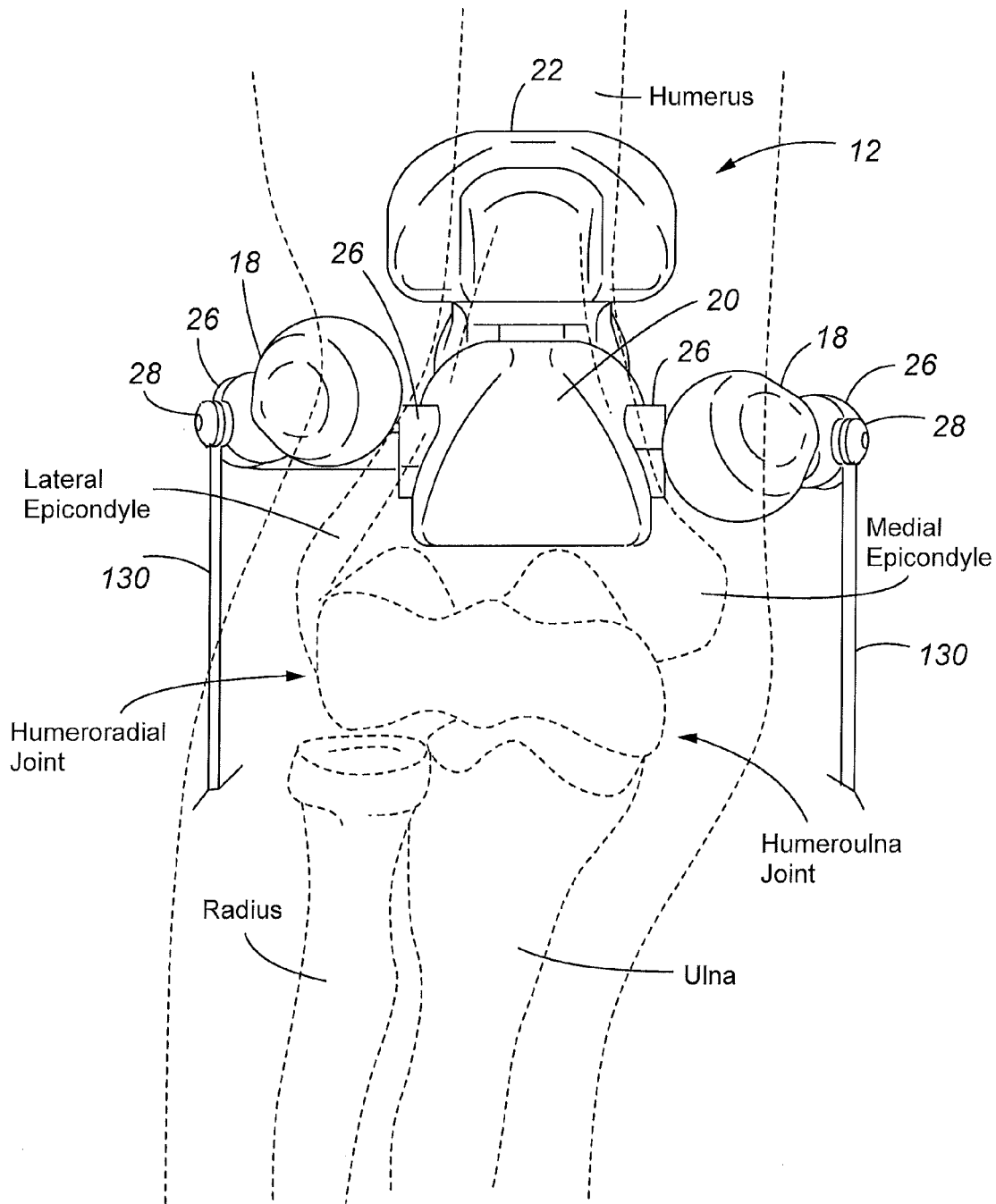
FIG. 6 is a front plan view of the lower arm or humeral cuff of one embodiment of the present invention positioned on a user arm and further showing as environment the skeletal structure of the user's arm and forearm.
Figure 7:
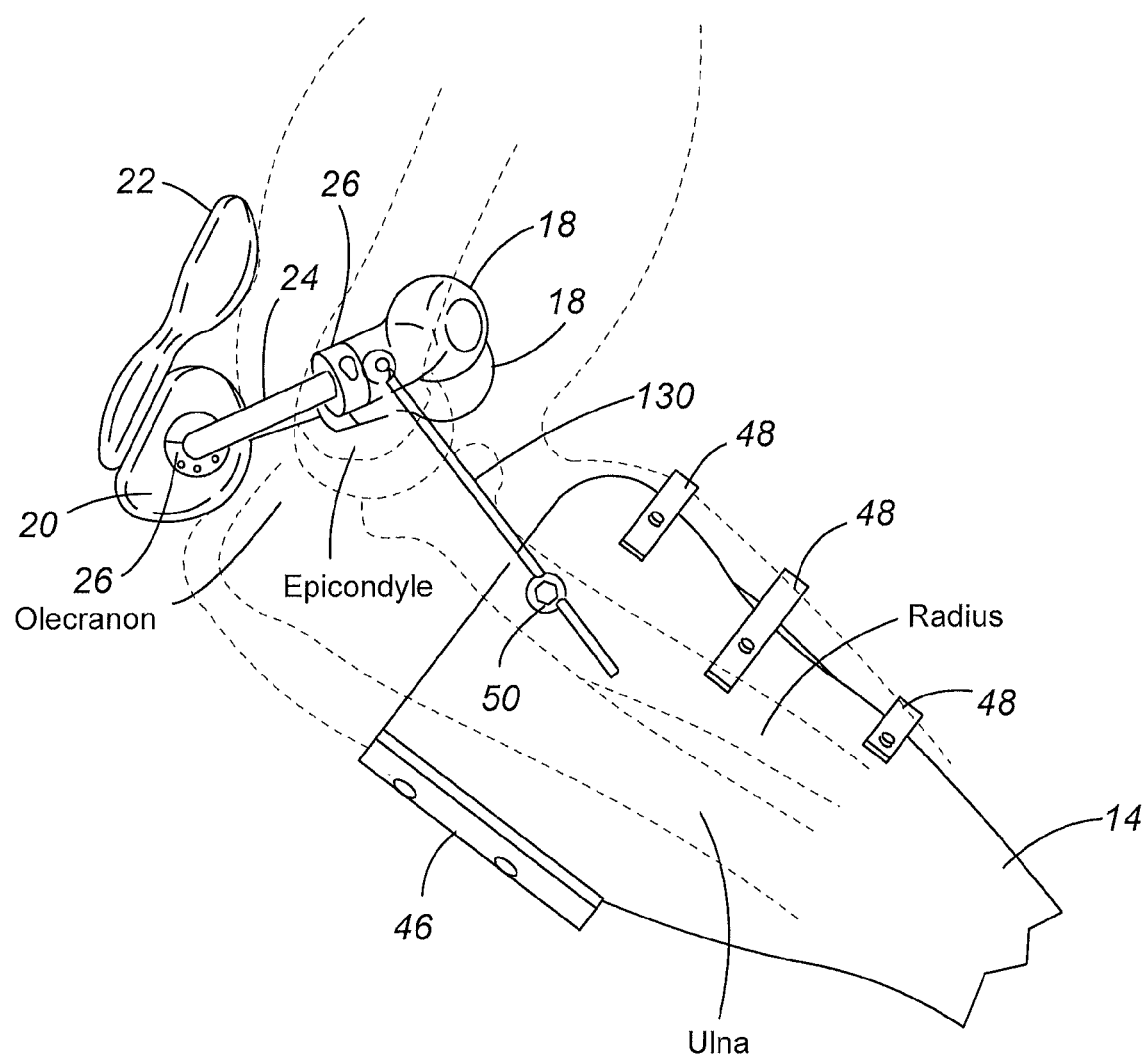
FIG. 7 is a side view of one embodiment of the prosthetic device of the present invention further showing as environment the skeletal structure of the user's arm and forearm.

Turning to FIGS. 6 and 7, the lower arm cuff 12 is shown as it would generally be positioned relative to the anatomy of an arm. The upper cuff 12 provides a suspension mount for the attached forearm section. As shown, the cuff 12 is worn on the lower arm so that the condyle contacts 18 are positioned to rest against and are thereby held in position against the distal humeral epicondyles of the elbow. More specifically as shown in FIG. 6, one of the condyle contacts 18 is positioned proximate the medial epicondyle, and the second opposed condyle contact 18 is positioned proximate the lateral epicondyle.

As best seen in FIG. 7, the posterior humeral contact 22 rests on the flared distal end of the humerus bone. The olecranon contact 20 is positioned to rest against the olecranon. This four-point contact provides a semi-rigid cuff which effectively creates a mechanical lock on the user's arm through an interference fit. The shape and adjustability of the components of the lower arm cuff prevents skin pinch and binding of adipose tissue during elbow flexion so as to maximize functionality and comfort.

Figure 11:
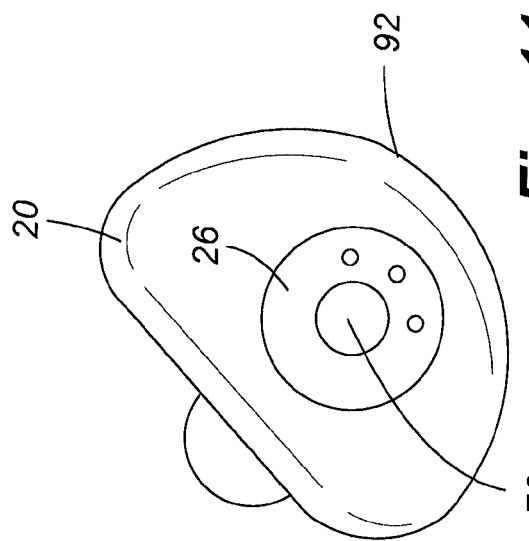
FIG. 11 is a side view of an olecranon contact of the present invention.
Figure 12:
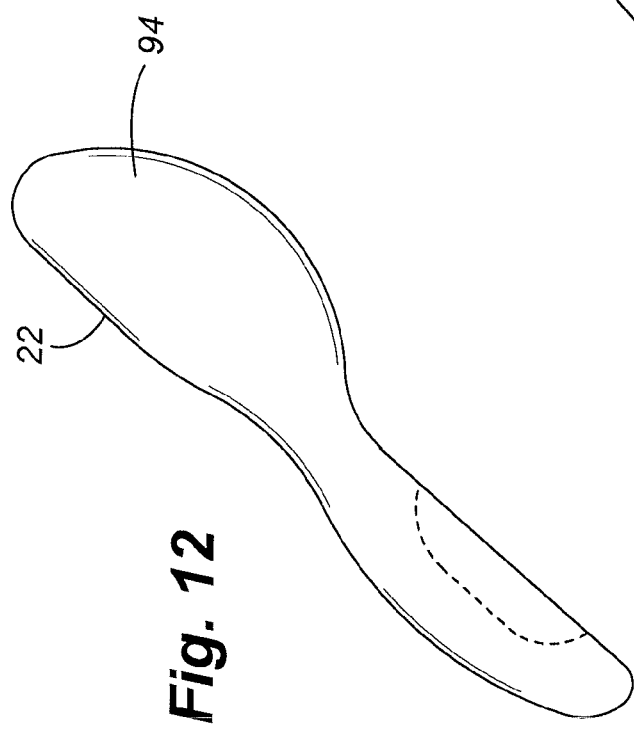
FIG. 12 is a side view of a posterior humeral contact of the present invention.

As previously noted, there are four shaft collars 26 associated with the lower arm cuff 12. An example of a shaft collar is shown in FIG. 8. The shaft collar comprises a generally c-shaped body and includes a threaded opening 72 extending through both halves or portions of the c-shaped body to receive a complementary threaded screw 74. The opening 76 in the center of the c-shaped body receives the bent rod 24, and by tightening of the threaded screw 74, the shaft collar may clamp and rigidly hold one end of the bent rod 24. Each shaft collar 26 further includes passages 78 to receive a threaded screw to interconnect the shaft collar 26 to the condyle contacts 18 and the olecranon contact 20. A representative example of this connection is shown in FIG. 9. As also shown in FIG. 9, each condyle contact 18 includes a bore or passage 80 to receive one end of the bent rod 24. Similarly, as shown in FIG. 10, the olecranon contact 20 includes a passageway 82 extending completely through the olecranon contact 20. Each passage 80 in the condyle contacts 18 has a length L1, and the total length of the passage 82 in the olecranon contact has a length L2. The passages 80 and 82 permit adjustable relative positioning of the condyle contacts 18 relative to the olecranon contact 20 by both adjusting the length of the bent rod within the respective passages 80 and 82, as well as permitting rotation of the bent rod 24 relative to the olecranon contact 20, and rotation of the condyle contacts 18 relative to the bent rods 24 to provide substantial adjustability relative to the size and shape of a residual limb. In addition, each of the condyle contacts is provided with a pad or cushion surface 18 for engagement with the arm of a wearer. Similarly, as shown in FIGS. 11 and 12, the olecranon contact 20 includes a padded portion 92, and the post-humeral contact 22 includes a padded portion 94. With reference back to FIG. 2, in a preferred embodiment, the padded portion 94 of the post-humeral contact 22 may further comprise a central raised and angled pad 96 for improved stability and engagement with the wearer's arm.

The shaft collars 26 affixed to the condyle contacts and olecranon contact allow for rotation and positioning for optimal adjustability, but are sufficiently strong to resist loading forces without movement. The medial and lateral condyle contact elements 18 rest upon the epicondyles on their respective sides of the wearer's arm as mentioned. The olecranon contact 20 presses on the posterior surface of the arm and down on the olecranon, and the posterior humeral contact 22 presses against the humeral bone. In combination the four contacts provide a stable and strong cuff for engagement with the residual limb. The cuff 12 can be adjusted to locate the position and orientation of the epicondyle contact points and to locate the position and orientation of the olecranon contact 20 and posterior humeral contact 22. The epicondyle feature locations may be varied in the sagittal, coronal and transverse planes in the following directions: ventral-dorsal, medial-lateral, and caudal-cranial. They may also be rotated about the axis of the olecranon contact 20. The performance of the cuff 12 is improved when these contacts are positioned to press mildly into the fossae (i.e., indentations) on either side of the bicep muscle. Adjusted in this manner, the cuff 12 provides maximum suspension-fixation, stability and comfort. Importantly, this adjustability also allows a single cuff design to be adjusted to operate on either a user's left hand or right hand side, meaning separate versions for opposite arms/hands are not necessary. This saves substantially on manufacturing costs and makes delivery and sizing easier.

Humeral fixation may also be modified by rotating the olecranon contact 20. This allows for increased or decreased contact with the humerus. As for example shown in FIG. 7, the olecranon contact 20 can be rotated either upward or downward to raise or lower the contact 20 along the humerus by adjusting the angular orientation of the curved rods 24. Axial downward loading of the cuff 12 produces a resultant torque that rotates the posterior humeral pad 94, 96 into the arm, further stabilizing the cuff 12 and giving rise to reaction forces at the condyles and the olecranon.

The condyle contacts 18, olecranon contact 20 and posterior humeral contact 22 may also be provided in different sizes, for example, small, medium and large. They may be interchanged to provide further flexibility. Further, these members may be interchanged with more compliant members as needed for individual applications. Similarly, the padded surfaces 90, 92 and 94 may be altered to provide contact members with a range of softness/hardness. In this way the rigidity of the cuff 12 may be modified to meet the sensitivity of each prospective user. The posterior humeral contact 22 may also be varied about the olecranon by adjusting the rods 24 into or out of the passageways 80 and 82. When suitably positioned, the shaft collars 26 may be set, causing the entire cuff to hold its preferred and functional shape in contact with the user's residual limb. Condyle contacts 18 are also interchangeable. The condyle contacts 18 in one embodiment are shaped similarly to large finger pads on the distal phalanges of the hands. In this manner, the condyle contacts 18 mimic grabbing hold of the arm with the hand, providing the mechanical equivalent of two fingers grasping the distal humerus. When the cuff 12 is used with a gauze sleeve or cloth padding, the pads 90 function as fingers with friction ridges. The contact portion 92 of the olecranon contact 20 and the contact portion 94, 96 of the posterior humeral contact 22 may be similarly shaped. The posterior contact 22 is shaped as a large thumb pad in the illustrated embodiment and the olecranon contact 20 is shaped as a pad and a humeral cup located at the elbow.

The cuff 12 may be adjusted to conform to work on residual limbs having different geometries (for example, varying radial and axial dimensions, varying curvature and varying combinations of hard and soft tissue). Compression can also be increased with healthy limits as desired for comfort, utility (varying weighted loads), and stability on the residual limb.

Figure 13:
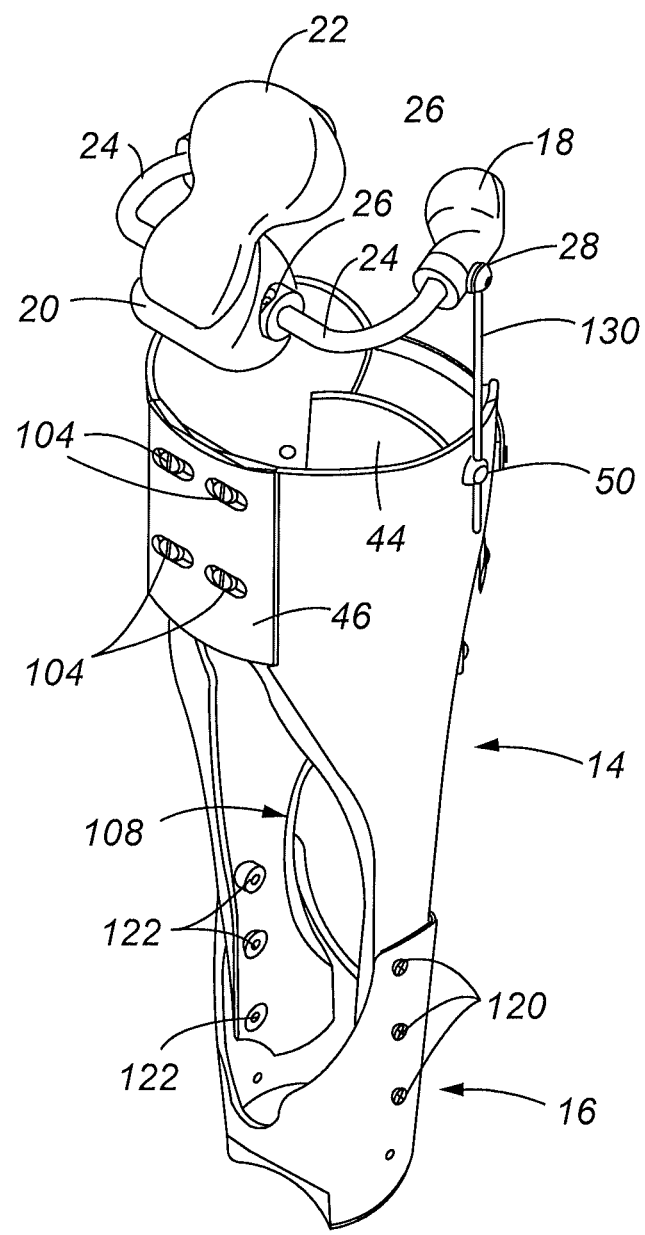
FIG. 13 is a rear perspective view of the embodiment of FIG. 1.

Turning now to FIGS. 1, 2 and 13, the forearm section 14 will be described in greater detail. The forearm section 14 grasps a forearm along its length following the radius and ulna bones. In use, the forearm half-shells 40, 42 are positioned and clamped about the residual limb below the elbow using perforated straps 48 having a series of spaced openings 100 which engage posts 102 formed on the surface of the half-shell forearm pieces 40, 42. Tension may be controlled by the user to ensure comfort which may be modified throughout the time period the prosthetic device is worn. A rear sizing plate 46 is further provided to secure the half-shells 40, 42 together. As illustrated, the rear sizing plate is provided with four elongated slots 104 which are positioned to overlie apertures 106 formed in the half-shells 40 and 42. A threaded boss and screw are positioned through the overlying apertures 106 and slots 104 and secured together to interconnect the half-shells 40 and 42 with the rear sizing plate 46. The threaded boss and screw (not shown) may be adjustably positioned along the length of the slots 104 to accommodate different sizes of a user's forearm.

As shown in FIGS. 1 and 13, the two half-shells 40 and 42 do not completely enclose the user's forearm. Rather, the half shells are shaped to provide an opening 108 to allow for heat dissipation as well as evaporation of sweat and moisture. As shown in FIG. 1, part of the opening 108 may be covered by the tongue 44. Similarly, additional openings may be formed in the half-shells 40 and 42 to provide further cooling and evaporative functionality. Further still, cutouts and outwardly formed bulges or reliefs may be formed in the half-shells 40 and 42 to provide contact pressure relief for arteries, veins and nerves, and to provide relief for adipose tissue to move with movement of the prosthetic device 12 without painful pinching. Indentations may also be located within the forearm half-shells 40 and 42 to provide specific contact points on the forearm. These indentations grasp remaining musculature and soft tissue. With reference to FIGS. 1, 2 and 13, a tongue 44 is shown as part of the forearm section assembly. The tongue 44 acts similar to the tongue on a shoe to facilitate placement of the forearm section 14 on the residual limb of a user and to act as a pad as needed. The tongue 44 as best shown in FIG. 13 opposes the rear sizing plate 46 and therefore provides additional surface area in contact with the limb for support.

The forearm half-shells 40 and 42 in preferred embodiments may include pockets for boney proximal and distal ulna extrusion and for soft tissue to move when compressed. The half-shells 40 and 42 are shaped to compress as a living hinge, with the axis along the posterior surface. The adjustable straps 48 are positioned along the anterior surface. As an alternative to adjustable straps, laces may be utilized or other means of adjustable securement as known to those of skill in the art. All of these methods allow for variable tension along the length of the forearm.

The forearm section 14 interfaces with the distal connector 16 in an adjustable manner. As best illustrated in FIG. 13, the outwardly projecting extensions or arms 60 and 62 of the distal connector include a series of axially aligned apertures that line up with axially aligned apertures formed in the half-shell forearm adapters 40 and 42. Accordingly, using a threaded boss and screw 120, the distal connector 16 may be interconnected to the forearm section 14 and the relative position between the two components may be adjusted to accommodate different axial lengths as needed. The slanted surface 64 of the distal connector 16 includes a standard 1/2-20 UNF threaded terminal attachment boss. The forearm section 14 and distal connector, in one embodiment, may be fabricated from polymer sheets, such as Kydex®, polypropylene, ABS or other thermal-formable polymer materials. The forearm section 14 and distal connector 16 are in one embodiment generally configured in a conical shape to permit accommodation over defined size ranges and allows the system to fit easily onto amputees without extensive customization. Anthropometric principles and data from the garment and clothing industry can be used to create basic interface designs over a family of sizes that will accommodate a majority of the population, for example, extra small, small, medium, large and extra large. The prosthetic device 10 can be used with a fabric sock or sleeve if desired and is either a permanent socket or temporary socket used for compressing residual limbs to substantially reduce post-trauma edema and foster wound healing. The open structure of the forearm section 14 and distal connector 16, together with the reduced interface afforded by the lower arm cuff 12, provides a structure which does not trap moisture, water, dirt, dust or other irritants against the skin, but rather permits them to be washed, wiped or evaporated away readily.

With reference to FIGS. 1, 4, 5 and 13, interconnection between the lower arm cuff 12 and the forearm section 14 will be described. As previously noted, each of the condyle contacts include a cable or rod connector 28 and each of the forearm half-shells 40 and 42 also include a cable or rod connector 50. The cables or rods 130 are affixed between the connectors to provide mechanical support and suspension for the forearm section 14 and distal connector 16. The cable 130 may be a flexible cable or a rigid rod. The connectors 28 and 50 are designed to rotate freely about their pivot attachment points through 360 degrees of motion. The connectors 50 in one embodiment are fabricated as a slotted receiver that engages the cable or rod 130 to clamp it while allowing for axial adjustment. The length of the cable bridging the user's elbow between the upper cuff 12 and the forearm section 14 may be shortened or lengthened as desired. The lateral and medial cable or rods 130 may be adjusted independently. The interface allows elbow flexion/extension of greater than 120 degrees and supination/pronation dependent on the user's remaining residual limb range of motion. Multiple candidate connection points, other than shown in the accompanying figures, are available at the proximal end of the forearm section 14 to permit positioning of the cable or rod between the lower arm cuff 12 and forearm section 14 as required by the needs of the individual user. Both the lower arm cuff 12 and the forearm section 14 contribute to the overall suspension of the device to hold the device securely and comfortably affixed to the user's residual limb under normal dynamic motion and loading. The components articulate around the user's elbow joint through mechanical cables or rods 130 that act together as a joint while supporting axial loading. Because of the adjustability of the prosthetic device, the user may adjust the device as necessary to facilitate different tasks throughout the day, including adjustments to accommodate light, moderate and heavy loading. The forearm section may also be fitted with cable guides to accommodate cables commonly used to operate body-powered hooks and terminal devices. The forearm section itself may be customized to allow for best fitting for the user. In FIG. 4 for example, a pair of holes 136 are formed to alleviate pressure at that location, and a bulge 140 is formed to have the section better conform to the shape of the wearer's residual limb.

Figure 14:
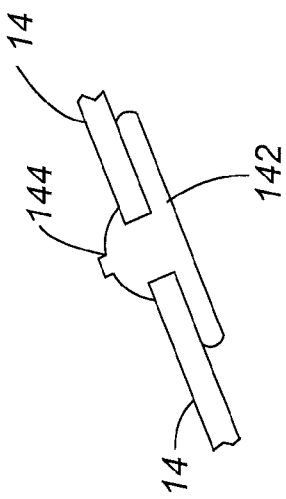
FIG. 14 is a section view of a portion of the forearm adapter including a contact pad.

Referring to FIG. 14, it is also contemplated that pads can be added to the interior surface of the forearm section in order have the section provide a most comfortable and supportive fit for the user. As shown in FIG. 14, a pad 142 is provided in which an aperture formed through the forearm section 14 facilitates attachment by a connecting tab 144 disposed on the opposite side of the forearm section. Alternatively, pads may be adhesively attached or attached by other mechanisms known to those of skill in the art.

Figure 15:
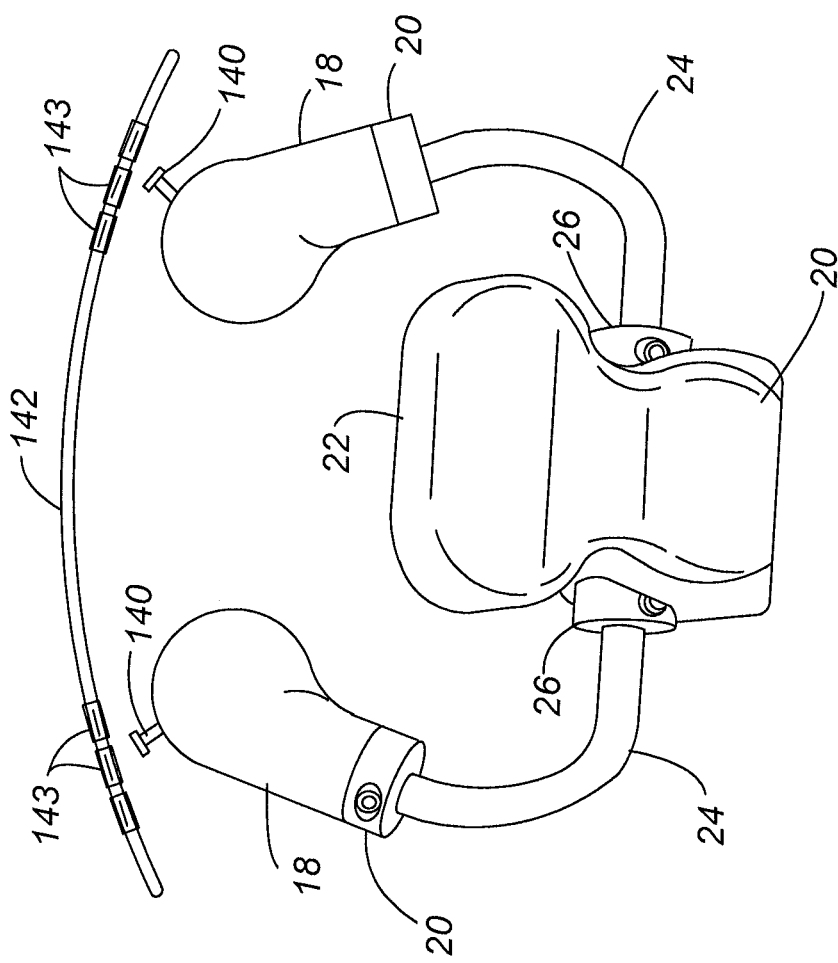
FIG. 15 is a perspective view of an embodiment of the lower arm cuff of the present invention further showing a security strap in association therewith.

As an alternative embodiment, a security strap may be secured between the condyle contacts 18. FIG. 15 illustrates one embodiment of such a security strap. Tabs 140 may be formed on the condyle contacts and used to secure a strap 142 having a plurality of slots 143 that are fitted over the tabs to secure the strap 142. The slotted strap would extend around the user's arm such that the upper cuff 12 is secured about the entire circumference of the user's lower arm.

Each component of the prosthetic device can be changed to provide equivalent function. Using materials with different properties allows performance to be enhanced to suit specific needs. Varying the geometry of the components will change the deflection of the prosthetic device 10 when it is tensioned. This deflection can be optimized to grasp the residual limb while achieving suspension and fixation. The interface or contact points between the condyle contacts, olecranon contacts and posterior humeral contacts can be changed and contoured to improve stability, suspension and fit.

Further still, the entire prosthetic device 10 may be encapsulated into an outer housing such that the components are not exposed to assist in keeping the unit clean. Such a housing could be produced with a more aesthetic or human-looking design. The upper extremity cuff 12 could be modified to grasp any structure on the human body. The contours and size of the component pieces can be shaped to grasp any extremity and provide suspension and fixation, under static and dynamic loads. The cable or rod 130 may be replaced with textile swathes to distribute loading and aid or replicate normal motion. These variations could be used to provide suspension at the shoulder for above-elbow amputees, at the hip for above-knee amputees, and at the knee for below-knee amputees. The interface provided by the prosthetic device described herein may also be modified to facilitate miniature motors or actuators and appropriate control methods to replace the manual means of adjusting the orientation and position of the components, for example, the medial lateral condyle contacts, cable or rod tension and posterior humeral contact. Included within the inventive concept is the use of more active components, for example, the use of servo-motors to move the condyle contacts 18 or the contact point for the olecranon. This could also include the use of active powered pneumatic or hydraulic systems that move features of the design to achieve comfort and stability, or inflating or deflating bladders to control how soft tissues are directed, contacted or pushed into relief areas, or to regulate how contact pressure is applied to the user's body. The embodiments described herein are also appropriate for veterinary applications.

The foregoing discussion of the invention has been presented for purposes of illustration and description. The foregoing is not intended to limit the invention to the form or forms disclosed herein. In the foregoing Detailed Description of the Invention for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description of the Invention, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights that include alternative embodiments to the extent permitted, including alternate, interchangeable and/or equivalent structures, functions, ranges or steps to those claimed.

What is claimed is:

1. A prosthetic device comprising:
an arm cuff having a plurality of contacts for contacting a residual limb of the wearer, said contacts comprising a pair of opposing condyle contacts, an olecranon contact, and a posterior humeral contact, said contacts providing four locations at which the residual limb is contacted;
a forearm section connected to said arm cuff, and comprising two shell sections, a tongue interconnecting one side of said shell sections, and a rear sizing plate interconnecting an opposite side of the shell sections; and
a distal connector connected to a distal end of said forearm section, said distal connector for connecting to a selected terminal device;
wherein said contacts provide a suspension mount to said forearm section.

2. A device as claimed in claim 1 wherein:
said olecranon contact and said posterior humeral contact form an integral base, and said condyle contacts extend away from said base.

3. A device as claimed in claim 2 wherein:
said arm cuff further comprises a pair of curved rods for interconnecting the condyle contacts to the base.

4. A device as claimed in claim 3, further including:
a shaft collar for connecting each of said curved rods to said base.

5. A device as claimed in claim 1, further including:
a pair of cables for interconnecting the arm cuff to the forearm section.

6. A device as claimed in claim 1, further including:
a plurality of adjustment straps for adjusting a spacing between said shell sections.

7. A device as claimed in claim 1 wherein:
said distal connector has an angled lower surface for orienting a terminal device for the wearer.

8. A device as claimed in claim 1 wherein said contacts are discrete contacts and provide a plurality of discrete contact points to enable adjustment to said residual limb.

9. A prosthetic device comprising:
means for attaching to an arm a plurality of supporting contacts to interconnect the arm to the prosthetic device, said means for attaching comprising a pair of opposing condyle contacts, an olecranon contact, and a posterior humeral contact, said contacts each making contact with the arm;
a forearm section connected to said means for attaching, and comprising two half shell sections, a tongue interconnecting one side of said half shell sections, and a rear sizing plate interconnecting an opposite side of the half shell sections;
a distal connector connected to a distal end of said forearm section, said distal connector for connecting to a selected terminal device;
wherein said means for attaching provide a suspension mount to said forearm section.

10. A device as claimed in claim 9 wherein:
said olecranon contact and said posterior humeral contact form an integral base, and said condyle contacts extend away from said base.

11. A device as claimed in claim 10 wherein:
said means for attaching further comprises a pair of curved rods for interconnecting the condyle contacts to said base.

12. A device as claimed in claim 11, further including:
a shaft collar for connecting each of said curved rods to said base.

13. A device as claimed in claim 9, further including:
a pair of cables for interconnecting the means for attaching to the forearm section.

14. A device as claimed in claim 9, further including:
a plurality of adjustment straps for adjusting a spacing between said half shell sections.

15. A device as claimed in claim 9 wherein:
said distal connector has an angled lower surface for orienting a terminal device for the wearer.

16. A device as claimed in claim 9 wherein said contacts are discrete contacts and provide a plurality of discrete contact points to enable adjustment to said arm.

17. A method of securing a prosthetic device to an arm of a wearer, said method comprising:
providing an arm cuff having a plurality of contacts for contacting the arm of the wearer, said contacts comprising a pair of opposing condyle contacts, an olecranon contact, and a posterior humeral contact, said contacts providing four locations at which the arm is contacted;
providing a forearm section connected to the arm cuff, and comprising two shell sections, a tongue interconnecting one side of said shell sections, and a rear sizing plate interconnecting an opposite side of the shell sections;
attaching one end of a distal connector to the forearm section; and attaching an opposite end of the distal connector to a terminal device;
mounting the arm cuff to the arm in which each of said contacts make contact with the wearer's arm thereby securing the prosthetic device to the arm; and wherein the posterior humeral contact rests on a flared distal end of a humerus of the wearer, the olecranon contact is positioned to rest against an olecranon of the wearer, one condyle contact is positioned to rest proximate a medial epicondyle of the wearer, and the other condyle contact is positioned to rest proximate the lateral epicondyle;
wherein said contacts provide a suspension mount to said forearm section.

18. A method as claimed in claim 17 wherein said contacts are discrete contacts and provide a plurality of discrete contact points to enable adjustment to said arm.

19. A prosthetic attachment for enabling attachment of a prosthetic device in a suspended configuration from a residual limb of a wearer comprising:
an arm cuff having a plurality of contacts for contacting a residual limb of a wearer, said contacts comprising a pair of opposing condyle contacts, an olecranon contact, and a posterior humeral contact, said contacts providing four locations at which the residual limb is contacted, said contacts providing a suspension mount to said prosthetic device;

wherein said contacts are discrete contacts and provide a plurality of discrete contact points to enable adjustment to said residual limb.

* * * * *